United States Patent
Yu

(10) Patent No.: US 7,141,400 B2
(45) Date of Patent: Nov. 28, 2006

(54) PRODUCTION OF BIODEGRADABLE THERMOPLASTIC MATERIALS FROM ORGANIC WASTES

(75) Inventor: Jian Yu, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 0 days.

(21) Appl. No.: 10/501,052

(22) PCT Filed: Jan. 15, 2003

(86) PCT No.: PCT/US03/01202

§ 371 (c)(1),
(2), (4) Date: Jun. 2, 2005

(87) PCT Pub. No.: WO03/062439

PCT Pub. Date: Jul. 31, 2003

(65) Prior Publication Data

US 2006/0088921 A1 Apr. 27, 2006

Related U.S. Application Data

(60) Provisional application No. 60/350,162, filed on Jan. 16, 2002.

(51) Int. Cl.
  *C12P 7/62* (2006.01)
  *C12P 39/00* (2006.01)
(52) U.S. Cl. .......................... 435/135; 42/42
(58) Field of Classification Search .............. 435/42, 435/135
See application file for complete search history.

(56) References Cited

U.S. PATENT DOCUMENTS

| | | | | |
|---|---|---|---|---|
| 4,800,021 A | * | 1/1989 | Desbos | 210/605 |
| 5,250,427 A | * | 10/1993 | Weaver et al. | 435/42 |
| 5,536,564 A | | 7/1996 | Noda | |
| 6,103,956 A | * | 8/2000 | Srienc et al. | 800/298 |
| 6,143,952 A | * | 11/2000 | Srienc et al. | 800/298 |
| 6,492,147 B1 | | 12/2002 | Imamura et al. | |
| 6,770,464 B1 | * | 8/2004 | Steinbüchel et al. | 435/134 |
| 2003/0201225 A1 | * | 10/2003 | Josse et al. | 210/605 |
| 2005/0011829 A1 | * | 1/2005 | Dong et al. | 210/603 |

* cited by examiner

*Primary Examiner*—Herbert J. Lilling
(74) *Attorney, Agent, or Firm*—Duane Morrin LLP

(57) ABSTRACT

A system and method for converting organic wastes to biodegradable thermoplastic materials including polyhydroxyalkanoates is disclosed, which method includes treating the organic wastes with an acidogenic microbial population to form fermentative organic acids, and polymerization of the organic acids by PHA-producing microbial species to form PHAs. The system includes a first compartment for acidogenesis of organic wastes without oxygen, and a second compartment, for polymer synthesis by enriched cultures of species with oxygen such as *R. eutropha, P. oleovorans*, or mixtures thereof. The compartments are integrated with barriers that permit mass transfer of organic acids while maintaining different culture conditions in the compartments.

7 Claims, 6 Drawing Sheets

PRODUCTION OF BIODEGRADABLE THERMOPLASTIC MATERIALS FROM ORGANIC WASTES

This application is a 371 of PCT/US03/01202 filed 01/15/2003 which claims benefit of 60/350,162 filed Jan. 16, 2002.

FIELD OF THE INVENTION

The present invention relates to systems and processes for producing biodegradable thermoplastic materials from various organic wastes.

BACKGROUND OF THE INVENTION

Polyhydroxyalkanoates (PHAs) are polyesters accumulated by many prokaryotic organisms as intracellular carbon and energy reserve materials under limited nutrients, such as nitrogen or phosphorous. PHA polymers demonstrate thermoplastic or elastic properties depending upon their particular composition. These materials have attracted interest because of their potential use as biodegradable alternatives to petroleum-based synthetic plastics such as polypropylene and polyethylene. Efforts have been made to produce PHAs by microbial fermentation on glucose and organic acids. The production of biodegradable thermoplastics from organic wastes can provide multiple benefits to the environment, and contribute to sustainable development.

Organic wastes are usually complex in nature, and cannot be directly utilized by PHA-producing microbes such as *Ralstonia eutropha*, a representative bacterium for PHA synthesis. Hydrolysis and acidogenesis is the first step in converting the wastes to short-chain fatty acids such as acetic, propionic and butyric acids, that can be further utilized by PHA-producing bacteria. At present, there are technological difficulties in coupling the waste acidogenesis and PHA synthesis steps. In essence, both acid-producing and PHA-producing cells can be cultivated in a mixed culture, and the acids released by the former are directly utilized by the latter. The PHA content of the solid mass, however, is not high enough (10–30% by wt.) for effective polymer recovery, due to the considerable amount of non-biodegradable matter in the waste, as well as the biomass of non-PHA producing microbes. Furthermore, a high acid concentration due to the high microbial activity of acidogenic microbes would inhibit the microbial activity of PHA-producing cells.

An improved system could contain two separate bioreactors, in order to satisfy the different physiologies and metabolic activities of the two types of microbes; one for acidogenesis of organic wastes, and a second for an enriched culture of PHA-producing strains, such as *R. eutropha*. The fermentative acids should preferably be transferred from the first reactor to the second reactor without causing a solid mixing between the two reactors, so that an enriched culture of *R. eutropha* with a high PHA content can be maintained in the second reactor. Furthermore, the acid accumulation and toxicity in the PHA-producing reactor would also be under control.

SUMMARY OF THE INVENTION

The present invention relates to a process and system for coupling the anaerobic digestion of food scraps with the production of polyhydroxyalkanoates (PHAs). The present invention makes use of molecule diffusion through barriers, and therefore does not require frequent foul cleaning, resulting in a reliable and efficient operation.

DESCRIPTION OF THE PREFERRED EMBODIMENTS

The present invention relates to a method and system for converting organic wastes to biodegradable polyhydroxyalkanoates (PHAs). The method comprises (a) treating the organic wastes with an acidogenic microbial population to form volatile organic acids; and (b) polymerization of the volatile organic acids by PHA-producing microbial species to form PHAs. The particular PHAs may comprise either short chain (3 to 5 carbon) monomers or long chain (6 to 14 carbon) monomers. The PHA-producing microbial species may be, e.g., *R. eutropha* or *P. oleovorans*. The viscosity-average molecular weight (Mv) of PHA polymers ranges from 50 to 100 kD.

The system for converting organic wastes to biodegradable PHAs comprises: (a) a first compartment, for acidogenesis of organic wastes without oxygen; and (b) a second compartment, for polymer synthesis by enriched cultures of *R. eutropha*, *P. oleovorans*, or mixtures thereof with oxygen. A barrier facility couples the first and second compartments. The compartments are characteristically bioreactors.

The present invention will be further described by the following examples.

EXAMPLES

Food scraps were collected from a local canteen, mixed with water in 1:1 (w/w), and blended to slurry. Anaerobic digestion of solid waste was conducted at 35° C. in a 5 L reactor with 3 L working volume. An inoculum for food waste acidogenesis was prepared by keeping food wastes under anaerobic conditions. The inoculum (25–30%, v/v) was mixed with fresh slurry to start anaerobic digestion. The slurry pH was first adjusted to 7.0 with 6 M NaOH, and raised to 7.0 after the pH dropped to about 5.0. No further pH control was implemented after the anaerobic digestion was coupled with PHA production.

Ralstonia eutropha ATCC 17699 was used for PHA production. The strain was maintained by monthly subculture on 2.0%-agar slants (pH 7.0) containing (per liter): 5 g yeast extract, 2.5 g beef extract, 5 g peptone and 5 g $(NH_4)_2SO_4$. The same nutrient-rich medium without agar was also used for seed culture. The seed was prepared in 2 L flasks containing 500 ml medium in a rotary shaker for 24 h at 200 rpm and 30° C. The cell mass was harvested and re-suspended in a mineral solution for PHA production. The mineral solution contained (per liter): 1.0 g $(NH_4)_2SO_4$, 5.8 g $K_2HPO_4$, 3.7 g $KH_2PO_4$, 0.4 g $MgSO_4$, and 1 mL microelement solution that contained (per liter of 1 M HCl): 2.78 g $FeSO_4.7H_2O$, 1.98 g $MnCl_2.4H_2O$, 2.81 g $CoSO_4.7H_2O$, 1.67 g $CaCl_2.2H_2O$, 0.17 g $CuCl_2.2H_2O$, and 0.29 g $ZnSO_4.7H_2O$.

Figure 1:
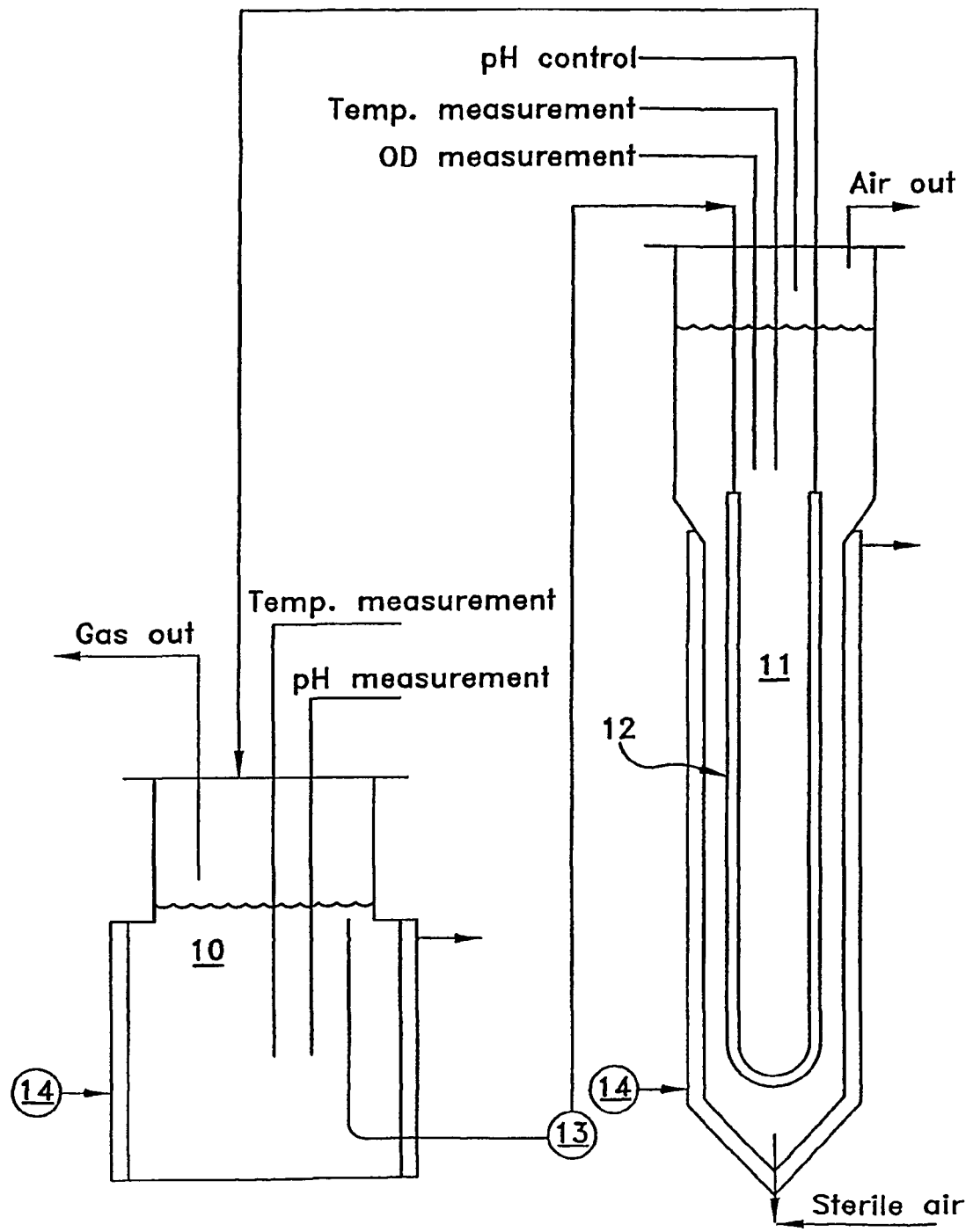
FIG. 1 is a diagram of the set-up of coupling the food scrap anaerobic digestion and PHA production.

PHA was synthesized by R. eutropha cells cultured in a 1.6 L air-bubbling bioreactor (Bioengineering AG, Switzerland) with 1.3 L working volume. FIG. 1 shows the setup that couples PHA production with anaerobic digestion of food scraps. The acidogenic slurry in reactor 10 (anaerobic digestion reactor) was cycled between the two reactors via a peristaltic pump 13 and a tubular barrier module 12 that was immersed in the mineral solution in reactor 11 (air-bubbling reactor). Under a concentration gradient across the barrier, the fermentative acids in the acidic slurry were transferred into the reactor 11 where they were utilized as the sole carbon source for PHA synthesis. Two types of barriers were used: A dense phase membrane made of silicone rubber (polysilozane) tubing (ID 3.2 mm, 1.6 mm or 3.2 mm wall thickness and 5 m in length), and a dialysis tubular membrane (cellulose) with nominal molecular weight cut-off (MWCO) of 6,000–8,000 (flat width 10 mm, 28 μm thickness and 0.23 m in length). The PHA-synthesis reactor was maintained at 30° C. via a water jacket and pH 7.5 by adding 3 M HCl or 3 M NaOH solution. The dissolved oxygen concentration was maintained at about 20% of air saturation with 3-vvm aeration. Further in FIG. 1, there is provided temperature control by the water bath 14.

PHA production from a mixture of pure butyric and lactic acids was conducted, as a control in a 2 L fermenter equipped with two six-bladed disk turbines. About 2.5 g cell mass of R. eutropha harvested from a nutrient-rich culture was re-suspended in 1.5 L mineral solution. A mixture of butyric acid (ca. 4 g/L) and lactic acid (ca. 4 g/L) was added into the mineral solution as the sole carbon source for PHA synthesis. The dissolved oxygen concentration was maintained above 20% air saturation with 1-vvm aeration and an agitation speed of 600 rpm. The cultivation temperature was controlled at 30° C. and the pH was controlled at 7.5 by adding 3 M HCl or 3 M NaOH solution. Cell growth was monitored by measuring the optical density (OD) at 620 nm.

Dry cell weight and PHA concentration were determined as follows: Thirty milliliters of culture broth was centrifuged at 10,000 g for 10 min and lyophilized to constant weight. PHA was extracted from the lyophilized cells in excess chloroform (10 mL chloroform for 0.2 g cell biomass) at 60° C. for 24 hours. The residual solid was removed by filtration through a glass filter and defined as the residual biomass. A PHA film was formed and its mass was weighed after the chloroform was completely vaporized at room temperature.

The PHA content was defined as the percentage of the PHA mass in the dry cell mass. Acetic acid, propionic acid and butyric acid were measured by gas chromatography equipped with a flame ionization detector by direct injection of acidified aqueous samples (pH 2 to 3) into a fused silica capillary column (+0.25 mm×25 m, Supelco, USA). Lactic acid was measured by high performance liquid chromatography equipped with a $C_{18}$ column and a UV Diode-array detector at 210 nm. The mobile phase was a 0.2% $H_3PO_4$ solution. The composition of PHA was determined after methanol esterification by GC-mass spectroscopy, a method developed by Lageveen et al.

Enzyme activities of amylase and lipase in a food scrap slurry were determined by using Amylase and Lipase-PS™ kits (Sigma, USA). The protease activity was measured with azocoll. One unit of protease activity was the amount of enzyme that catalyzed the release of azo dye and gave an absorbance change of 0.001/min at 520 nm.

The molecular size of PHA polymers was measured based on viscosity measurement to give a viscosity-average molecular weight, Mv.

Figure 2:
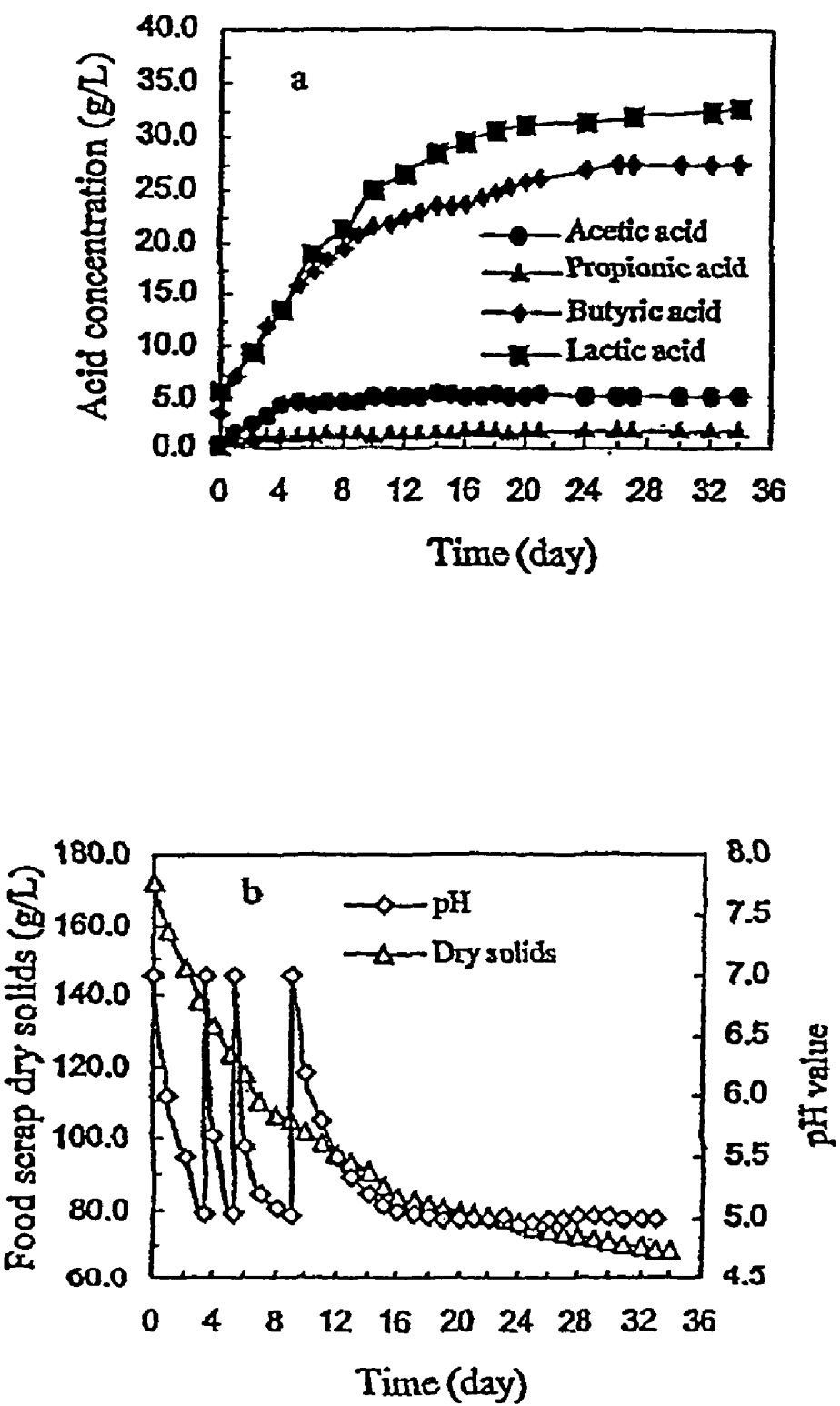
FIG. 2 are graphs of time courses of food scrap digestion under anaerobic conditions (a: formation of four major fermentative acids; b: solid waste digestion, pH change and control)

FIG. 2 shows the time courses of batch digestion and acidification of food scraps under anaerobic conditions. Four organic acids were detected as the major fermentative products. Among them, lactic acid and butyric acid were the two major acids, and their concentrations reached 32.6 g/L and 27.4 g/L after 20 days. About 5.5 g/L of acetic acid and 1.8 g/L of propionic acid were accumulated in anaerobic digestion but kept at quite constant levels for most of the time (FIG. 2a).

The initial slurry had a solid content of 172 g/L, and 60.3% (w/w) or 103.7 g/L was digested in 34 days. The solid mass declined quickly in the first 7 days, and more than 59.5% of the digestible food scraps were consumed during this period of time. The pH dropped rapidly from 7.0 to below 5.0 due to the accumulation of large amounts of organic acids. The pH was adjusted back to 7.0 three times in the first 10 days. After that, the pH was not adjusted because of a much slower pH decline or acid release rate. The acidic slurry was cycled through the tubular barrier module (12 in FIG. 1). Since the acid molecules were transferred through the barrier into the polymer-producing reactor (11 in FIG. 1) and utilized by R. eutropha cells, the pH in the anaerobic digestion reactor (10 in FIG. 1) was controlled. About 13.7% of the digestible food scraps were digested in the last 17 days (FIG. 2b). The slowdown of solid digestion was not only attributed to the low pH level, but also to the residual solids that became difficult to digest. This indicated that most of the easily digestible components in food scraps were quickly consumed in the early stage. After the acid concentrations reached almost constant levels at the $17^{th}$ day, the acidic slurry was cycled through the barrier module 12 immersed in the PHA-producing reactor 11 for PHA synthesis.

Figure 3:
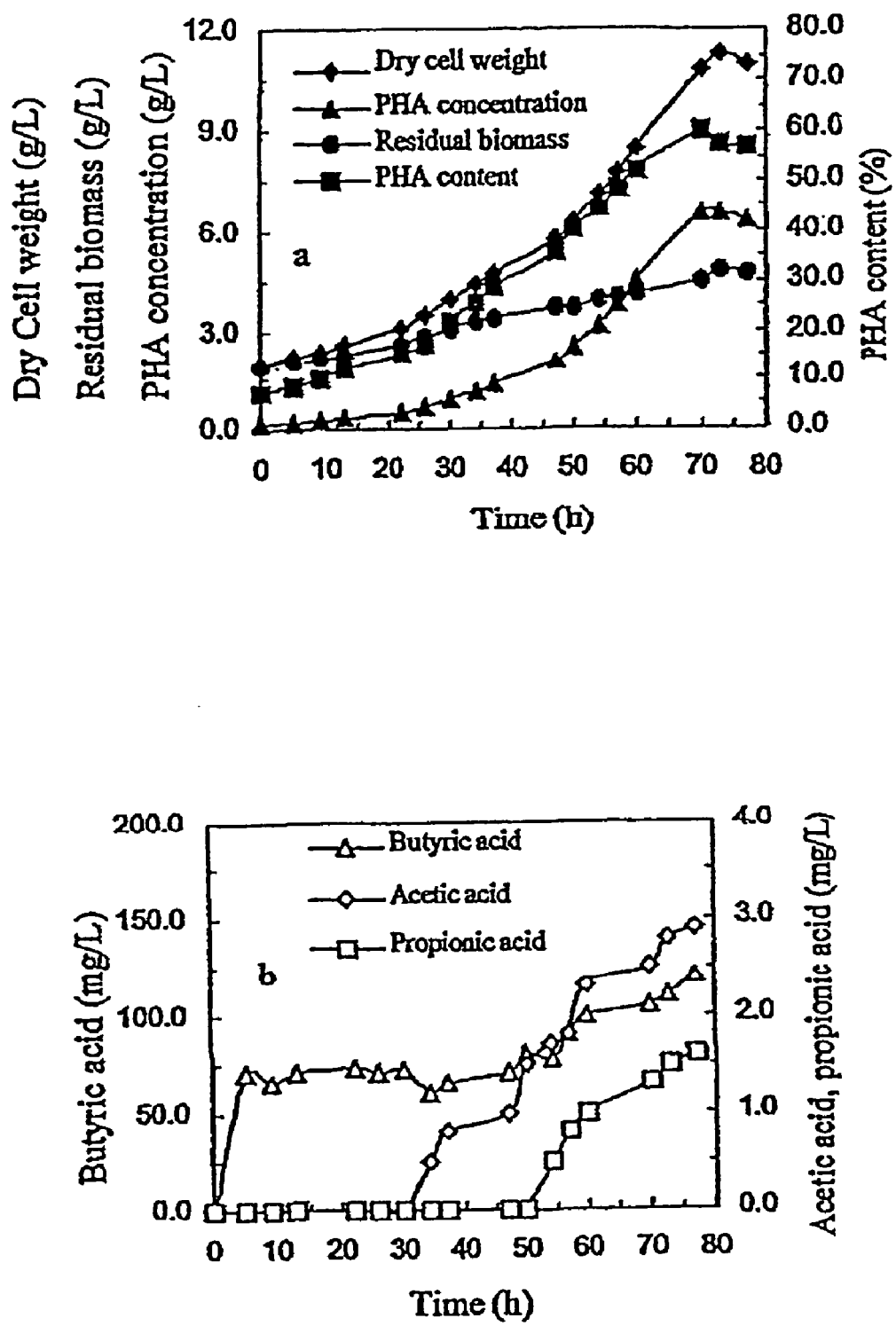
FIG. 3 are graphs of time courses of PHA formation with the silicon-dense membrane (a: growth of *R. eutropha* and PHA synthesis on the fermentative acids transferred from the acidic slurry through the dense membrane; b: the organic acids detected in the mineral solution of the PHA-producing reactor)

PHA production coupled with anaerobic digestion of food scraps was conducted in the air-bubbling reactor 11 with two types of barriers; dense phase membrane and dialysis membrane. FIG. 3 shows the time courses of PHA production when the dense phase membrane was used for acid transfer from the acidic slurry. The residual biomass was increased from 1.9 g/L to 4.5 g/L in 73 hours. The PHA content and PHA concentration reached 60.2% and 6.5 g/L in 70 hours, respectively (FIG. 3a). This means that the acids in the acidic slurry were transferred to the cells of R. eutropha through the silicone dense phase membrane and used as the sole carbon source for cell growth as well as PHA accumulation. Acetic, propionic and butyric acids were detected in the culture broth of R. eutropha at different times, which depended on their relative rates of mass transfer through the membrane and consumption by R. eutropha of individual acids (FIG. 3b). Butyric acid was the major fermentative acid and its concentration was below 120 mg/L in the mineral solution. Its transfer rate was the fastest due to its highest concentration difference across the barrier. Acetic acid and propionic acid appeared in the late stage, and their concentrations reached 3.0 mg/L and 1.6 mg/L, respectively. Compared with the acid concentrations in the acidic slurry, the acid concentration differences across the dense phase membrane were 27.4 g/L (butyric acid), 5.5 g/L (acetic acid), and 1.8 g/L (propionic acid), respectively. No lactic acid was detected in the PHA-producing reactor even though its concentration difference across the membrane was up to 32.6 g/L.

Figure 4:
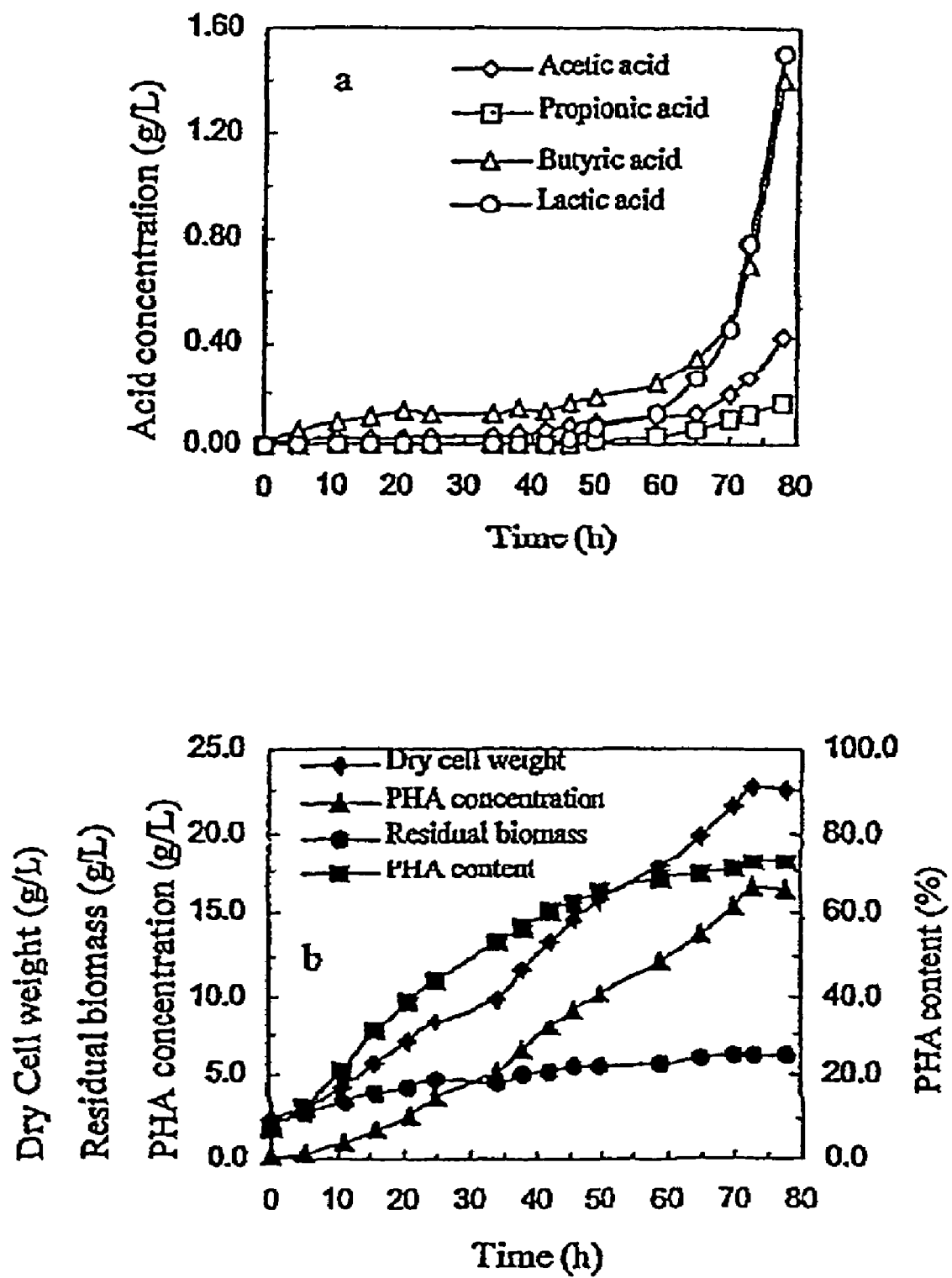
FIG. 4 are graphs of time courses of PHA production with the dialysis membrane (a: the organic acids detected in the mineral solution of PHA-producing reactors; b: growth of *R. eutropha* and PHA synthesis on the fermentative acids transferred from the acidic slurry through the dialysis membrane.
Figure 5:
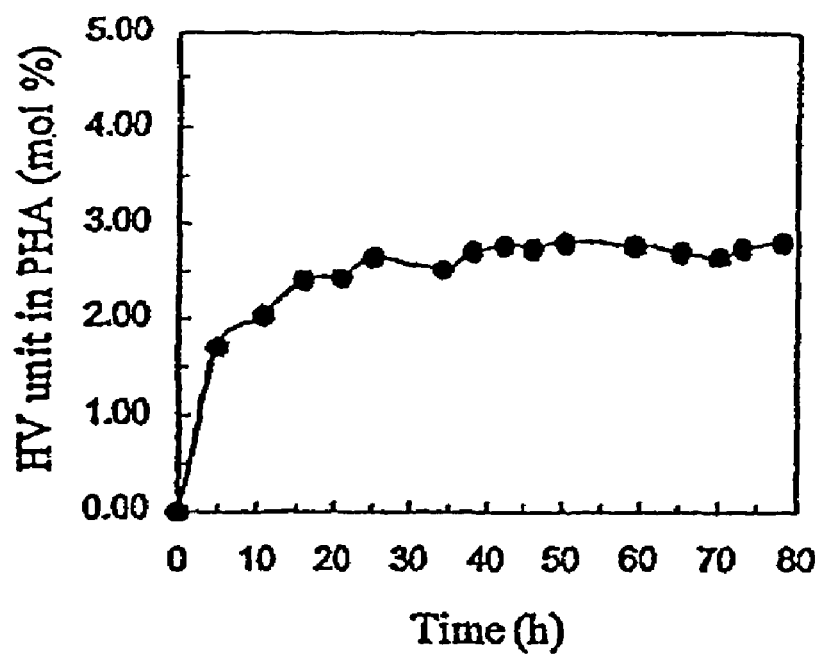
FIG. 5 is a graph of the mole percentage of hydroxyvalerate (HV) monomer in the copolymer of poly(hydroxybutyrate-co-hydroxyvalerate) synthesized from the fermentative acids transferred from the dialysis membrane.

FIG. 4 shows the PHA production when the dialysis membrane was used as a barrier between acidogenesis and PHA production. Both acetic acid and butyric acid were detected in the early stage in the PHA-producing reactor, while lactic acid and propionic acid were detected after 40 hours. Different from FIG. 3b, lactic acid was also transferred through the dialysis membrane in addition to the three volatile fatty acids. Moreover, the concentrations of four acids in the PHA-producing reactor (11 in FIG. 1) were much higher than those from the dense phase membrane. After 60 hours, the acid concentrations rose quickly because of the slowdown of PHA synthesis. The concentration of acetic, propionic, butyric and lactic acids in the broth of polymer synthesis reached 0.42, 0.16, 1.40 and 1.51 g/L, respectively (FIG. 4a). With a large amount of organic acids being transferred through the dialysis membrane, PHA was accumulated quickly in polymer-producing cells. PHA content and PHA concentration reached 72.6% and 16.5 g/L in 73 hours, respectively (FIG. 4b). They were much higher than those (60.2%, 6.5 g/L) in FIG. 3a. The dry cell mass reached 22.7 g/L in 73 hours, which was two times higher than the value (11.3 g/L) obtained with the dense membrane. Furthermore, the obtained PHA was a copolymer of hydroxybutyrate (HB) and hydroxyvalerate (HV). The HV unit that was synthesized from propionic and acetic acids was detected in PHA and its mole fraction was about 2.8% during most of the fermentation time (FIG. 5). In contrast, no HV unit was detected in the PHA obtained with the silicone dense phase membrane, even though a small amount of propionic acid (1.6 mg/L) was detected in the culture broth (FIG. 3b).

Figure 6:
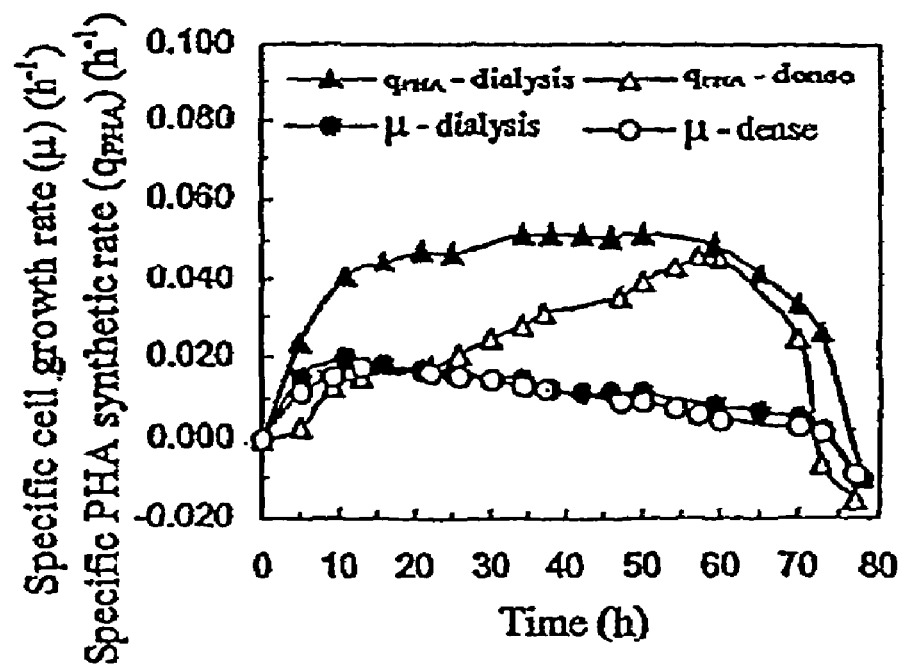
FIG. 6 is a graph of the specific PHA synthetic rates and specific cell growth rates with the dense membrane and the dialysis membrane.

FIG. 6 compares the specific cell growth rates ($\mu$) and specific PHA synthetic rates ($q_{PHA}$) of R. eutropha with the two types of barriers. The specific cell growth rates were very similar with both dense phase and dialysis membranes and reached 0.018 $h^{-1}$ at 16 h and 0.020 $h^{-1}$ at 11 h, respectively. The specific PHA synthetic rates, however, were very different. The specific PHA synthetic rate with the dense membrane increased slowly and reached the maximum value 0.047 $h^{-1}$ at 70 h, while with the dialysis membrane, the specific PHA synthetic rate reached the high value quickly, resulting in the accumulation of a large amount of PHA in cells, even in the early stage of PHA synthesis.

During food scrap digestion, the pH dropped due to the accumulation of large amounts of organic acids, and the digestion rate was influenced by the change of pH, that in turn affected the enzymatic activities of solid hydrolysis. Table 1 shows the activities of three major extracellular enzymes useful in the hydrolysis of food scraps at different pH levels in the first 14 days. It is apparent that enzyme activities depended on the pH level, the amylase for starch hydrolysis and the lipase for fat hydrolysis in particular.

TABLE 1

Enzyme activities at different pH levels during anaerobic digestion of food scraps

| | pH | | | | | |
|---|---|---|---|---|---|---|
| | 6.8 | 6.5 | 6.0 | 5.7 | 5.3 | 5.0 |
| Amylase activity (u/L) | 84.0 | 77.3 | 70.5 | 54.8 | 30.4 | 17.3 |
| Lipase activity (u/L) | 38.9 | 37.4 | 36.3 | 35.7 | 23.1 | 13.9 |
| Protease activity (u/L) | 10.7 | 12.4 | 24.1 | 15.2 | 22.1 | 20.5 |

Amylase and lipase showed high activities at neutral pH levels; protease showed high activity at low pH levels. This points to the fact that starch and oily matter in food scraps were quickly hydrolyzed at neutral pH, and protein hydrolysis was accelerated at low pH, releasing amino acids as nutrients. A pH swing between the neutral and acidic levels, therefore, enhances the food scrap digestion, compared to a constant pH level. In the first 14 days, most of the easily digestible solids had been used and the microbial activity declined. The enzymatic activities even at a neutral pH level became low (10–15 u/L), compared to 40-80 u/L at the beginning of anaerobic digestion.

Acid mass transfer from the acidic slurry to the PHA synthesis medium was essential to the coupling of the two reactors. The mass transfer rates of organic acids affected not only the PHA synthesis but also the food scrap digestion, because the pH could be controlled with continuous removal of the organic acids. PHA production is dependent on the carbon source provided, and, to some extent, more PHA could be synthesized with more acids being transferred from the acidic reactor at a faster rate. The continuous removal of the accumulated acids in the acidic slurry could also raise the enzyme activity such as amylase and lipase for hydrolysis of food scraps.

The mass transfer of the small molecules of organic acids relies on molecular diffusion in the barriers, and hence, the barrier structure has a significant effect on the diffusion rate. Table 2 shows the transfer rates of four organic acids in two media (water versus food scrap slurry) through two types of barriers (dense phase vs. dialysis). For the dense phase membrane, the effect of the membrane thickness on the transfer rate was compared by using the same membrane with different thicknesses (3.2 mm vs. 1.6 mm). The transfer rates of the acids were almost doubled when the membrane thickness was decreased from 3.2 mm to 1.6 mm (Nos. 1 and 2 in Table 2). The rates are proportional to the reciprocal of the membrane thickness. With the dense phase membrane and the same concentration gradients across the membrane, the acid transfer rates were also affected by the molecular size and polarity of the acids (No. 3 in Table 2). The relatively long aliphatic chain in butyric acid gave the acid the highest solubility in the dense phase membrane, and hence, the highest diffusion rate which was followed by propionic and acetic acids (No. 3 in Table 2). This points to the fact that the transfer rates of volatile fatty acids in the dense phase membrane were affected by both acid solubility as well as molecular diffusion within the membrane. The solubility of a particular acid determines to a great extent its transfer rate in the dense phase membrane. Because lactic acid, with an extra hydroxyl group on its a carbon, has a higher polarity than propionic acid, its solubility is much lower in the silicone membrane, and a negligible mass transfer is observed. For the dialysis membrane, a different mass transfer mechanism of acid molecules was observed. Theoretically, all the small molecules (MW≦MWCO) can defuse through the membrane regardless of their ionic or free molecule forms. The dialysis rates of acetic, propionic and butyric acids through the dialysis membrane were increased by 1298, 448 and 225 times, respectively, compared with those in the dense phase membrane (No. 4 & No. 6 in Table 2). Furthermore, lactic acid, which could not be transferred in the dense phase membrane, was also quickly transferred through the dialysis membrane. Surface fouling or microbial attachment on a membrane surface is a ubiquitous phenomenon when the surface is in contact with microbial cells and slurry, which may reduce the mass transfer rate and cause frequent non-production cleaning. Comparing the mass transfer rates of the organic acids in the food scrap slurry and water solution indicates a negligible effect of surface fouling on the rate in the two types of barriers. Acids in water and in slurry had similar dialysis rates (No. 2 & No. 4 for the dense phase membranes and No. 5 & No. 6 for the dialysis membrane.)

TABLE 2

Dialysis rates of organic acids in two media through two dense phase membranes and one dialysis membrane

| | | Acid dialysis rates (mmol/sec/m$^2$) | | | |
|---|---|---|---|---|---|
| No. | Membranes/media | Acetic acid | Propionic acid | Butyric acid | Lactic acid |
| 1 | Dense membrane$^A$ (3.2 mm thickness) | 1.05E−5 | 1.14E−5 | 2.96E−4 | 0 |
| 2 | Dense membrane$^A$ (1.6 mm thickness) | 1.94E−5 | 2.25E−5 | 6.16E−4 | 0 |
| 3 | Dense membrane$^B$ (1.6 mm thickness) | 9.72E−5 | 1.24E−4 | 6.07E−4 | 0 |
| 4 | Dense membrane$^C$ (1.6 mm thickness) | 2.01E−5 | 2.14E−5 | 6.21E−4 | 0 |
| 5 | Dialysis membrane$^A$ | 2.52E−2 | 1.07E−2 | 0.135 | 0.147 |
| 6 | Dialysis membrane$^C$ | 2.61E−2 | 9.59E−3 | 0.140 | 0.154 |

Liquid media:
$^A$Water solution (pH 5), and acetic, propionic, butyric and lactic acids are 5, 2, 25 and 30 g/L, respectively.
$^B$Water solution (pH 5), and acetic, propionic, butyric and lactic acids are 25 g/L, respectively.
$^C$Food waste slurry (pH 5), and acetic, propionic, butyric and lactic acids are 5.45, 1.84, 25.7 and 31.6 g/L, respectively.

Individual organic acids including acetic acid, propionic acid, butyric acid and lactic acid have been used by *R. eutropha* as the carbon source for PHA production. From the anaerobic digestion of organic wastes, a mixture of fermentative acids was usually obtained. Furthermore, the composition of acid mixture in the polymer-producing reactor for PHA synthesis was determined by the types of barriers used for reactor coupling. With the dense phase membrane, butyric acid was the major acid transferred, and the PHA formed was a homopolymer (e.g., poly(3-hydroxybutyrate), PHB) or copolymers (e.g., poly(3-hydroxybutyrate-co-3-hydroxyvalerate), PHBV). With the dialysis membrane, the acid mass transfer rates were greatly improved, and the transferred acids were a mixture of acetic, propionic, butyric and lactic acids. Due to the improvement in mass transfer of propionic acid with the dialysis membrane, the hydroxyvalerate (HV) monomer was synthesized from propionic acid and acetic acid by *R. eutropha* and became a measurable monomeric unit in PHA. Since the copolymer of hydroxybutyrate and hydroxyvalerate had more desirable material properties than PHB, the HV content of copolymer can be controlled by encouraging more propionic acid production in the acidogenesis reactor.

Figure 7:
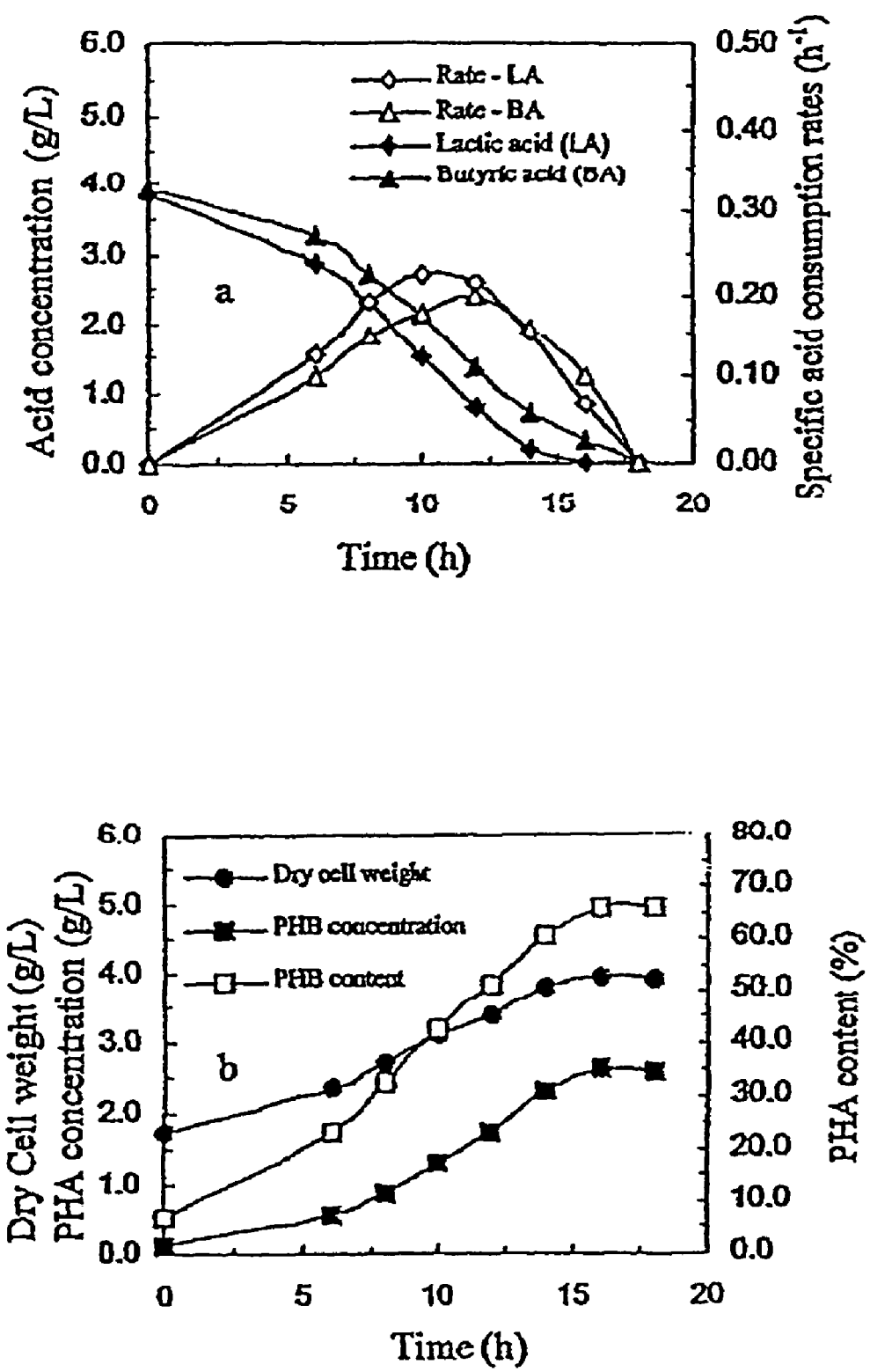
FIG. 7 are graphs of time courses of a batch culture of *R. eutropha* on a binary mixture of pure butyric acid and lactic acid (a: the acid concentrations and the specific consumption rates; b: growth of *R. eutropha* and PHA synthesis on the mixed acids).

Because butyric acid and lactic acid are the major acids from the food scrap digestion, their mass transfer rates were five to six times higher than that of acetic acid and fifteen to sixteen times higher than that of propionic acid in the dialysis membrane. Thus, butyric acid and lactic acid were the major substrates that appeared in the polymer-producing reactor for cell growth and PHA production. The culture of *R. eutropha* on individual butyric acid or lactic acid showed that both acids were an appropriate carbon source for PHA synthesis. The maximum cell biomass and PHA content were achieved at their concentrations at around 10 g/L, and no considerable acid inhibition was observed at this concentration level. FIG. 7 further shows the batch culture of *R. eutropha* on a binary mixture of pure butyric acid and lactic acid. Butyric acid and lactic acid were utilized almost simultaneously, with lactic acid being used faster than butyric acid. The maximum specific consumption rates of butyric acid and lactic acid reached 0.20 h$^{-1}$ at 12 h and 0.23 h$^{-1}$ at 10 hours, respectively (FIG. 7a). The dry cell mass and PHA content reached 3.98 g/L and 66.1% at 16 hours, respectively (FIG. 7b). The formed polymer was a homopolymer (PHB). This suggests that the mixture of butyric acid and lactic acid is a good carbon source for PHA synthesis, but unlike propionic acid, lactic acid cannot be used for synthesis of hydroxyvalerate (HV) monomer, even though both acids have three carbons.

By utilizing the system and process of the present invention, organic acids are continuously released from anaerobic digestion of food scraps and transferred across a barrier for PHA synthesis. Because there are no solid mixing and hydraulic washout of cells, an enriched culture of PHA synthesis can be maintained to produce a biomass of very high PHA content. The 72.6% (w/w) PHA achieved is a high polymer content obtained from organic waste treatment and comparable to the polymer content obtained from pure glucose fermentation. The high polymer content is the prerequisite to develop a downstream process for cost-effective polymer recovery from cell mass. Thus, the present invention demonstrates that organic wastes can be utilized for valuable products.

Table 3 shows the viscosity-average molecular weight (Mv) of PHA polymers produced under controlled carbon-nitrogen weight ratios (C/N).

TABLE 3

Viscosity-average Molecular Weight (Mv) of PHA Biopolymers formed on Organic Acids under Initial Carbon/Nitrogen ratio (C/N)

| | C/N | | | | |
|---|---|---|---|---|---|
| | 4 | 9 | 30 | 45 | 72 |
| Mv (kD) | 820 | 830 | 730 | 580 | 510 |

What is claimed is:

1. A method of converting organic wastes to biodegradable thermoplastic materials including polyhydroxyalkanoates (PHAs) which comprises:
   (a) treating the organic wastes with an acidogenic microbial population in a first compartment to form volatile organic acids; and
   (b) polymerizing the volatile organic acids by polyhyciroxyalkanoate (PHA) producing microbial species in a second compartment to form PHAs, wherein the volatile organic acids are transferred from the first to the second compartments via molecule diffusion across barriers.

2. The method as recited in claim 1, wherein the PHA producing microbial species are *R. eutropha* or *P. oleovorans*.

3. The method as recited in claim 1, wherein (a) occurs in an anaerobic environment and (b) occurs in an aerobic environment.

4. The method as recited in claim 1, wherein the PHAs contain 3 to 5 carbon monomers.

5. The method as recited in claim 1, wherein the PHAs contain 6 to 14 carbon monomers.

6. The method as recited in claim 1, wherein the PTIA is poly(3-hydroxybutyrate) or poly(3-hydroxybutyrate-co-3-hydroxyvalerate).

7. The method as recited in claim 1, wherein the compartments are bioreactors.

* * * * *